US 8,815,172 B2

(12) United States Patent
Hanada (10) Patent No.: US 8,815,172 B2
(45) Date of Patent: Aug. 26, 2014

(54) INSTALLATION APPARATUS AND STERILIZING APPARATUS AND METHOD

(71) Applicants: Canon Marketing Japan Kabushiki Kaisha, Tokyo (JP); Elk Corporation, Osaka (JP); Kabushiki Kaisha Elquest, Chiba (JP)

(72) Inventor: Yasushi Hanada, Chiba (JP)

(73) Assignees: Canon Marketing Japan Kabushiki Kaisha, Tokyo (JP); Elk Corporation, Osaka (JP); Kabushiki Kaisha Elquest, Chiba (JP)

( * ) Notice: Subject to any disclaimer, the term of this patent is extended or adjusted under 35 U.S.C. 154(b) by 0 days.

(21) Appl. No.: 13/645,186

(22) Filed: Oct. 4, 2012

(65) Prior Publication Data

US 2013/0101467 A1    Apr. 25, 2013

(30) Foreign Application Priority Data

Oct. 6, 2011   (JP) ................................. 2011-222132

(51) Int. Cl.
*A61L 2/00*   (2006.01)
*A61L 2/16*   (2006.01)
*A61L 2/28*   (2006.01)

(52) U.S. Cl.
CPC ..... *A61L 2/16* (2013.01); *A61L 2/28* (2013.01)
USPC ............... 422/292; 422/119; 422/26; 422/28; 312/31

(58) Field of Classification Search
CPC .................................... A61L 2/16; A61L 2/28
USPC .................. 422/292, 119, 26, 28; 312/31
See application file for complete search history.

(56) References Cited

U.S. PATENT DOCUMENTS 3,561,918 A * 2/1971 Ray ............................... 422/119
2003/0152480 A1   8/2003 Sham

FOREIGN PATENT DOCUMENTS

| JP | H10272170 A | 10/1998 |
| JP | H11226095 A | 8/1999 |
| JP | 2005-176939 A | 7/2005 |
| JP | 2005176939 A | 7/2005 |

* cited by examiner

*Primary Examiner* — Lyle Alexander
(74) *Attorney, Agent, or Firm* — Canon USA, Inc. IP Division (57) ABSTRACT

The application relates to apparatus capable of easily mounting an indicator to a device for verifying a sterilizing effect when a sterilizing process is performed. An installation apparatus is disclosed for positioning a sterilization verifying device in a sterilizing chamber having a sterilizing chamber door, said sterilization verifying device comprising a containing chamber for containing an indicator, the containing chamber having an opening for receiving an indicator into the chamber and connected to an introduction tube for introducing a sterilizing gas into the containing chamber, the installation apparatus comprising arrangement means configured to, in a case that the sterilizing chamber door is closed, position the opening of the containing chamber with respect to an inner wall of the sterilizing chamber door, such that the inner wall and the opening are brought into contact with each other thereby sealing the containing chamber against the inner wall.

11 Claims, 8 Drawing Sheets

FIG.6

INSTALLATION APPARATUS AND STERILIZING APPARATUS AND METHOD

BACKGROUND OF THE INVENTION

1. Field of the Invention

The present invention relates to an installation apparatus of a sterilization verifying device and an installation method.

2. Description of the Related Art

It is preferable that a sterilizing effect is verified in an object for sterilization to verify the sterilizing effect inside the object, but conventionally it is practically impossible to mount an indicator capable of verifying a sterilizing effect into an object for sterilization. Thus, a device for creating a virtual environment which is similar to an interior environment of the object for sterilization to verify a sterilizing effect is used.

Japanese Patent Application Laid-Open No. 2005-176939 discusses a technology for mounting an indicator to a device for verifying a sterilizing effect. Specifically the technology is for mounting an indicator into an indicator case from a cap of an end of the indicator case. In Japanese Patent Application Laid-Open No. 2005-176939, the device for verifying a sterilizing effect is a precision instrument, and thus in order to replace an indicator, a part for mounting the indicator of the device needs to be opened to mount the indicator and finally the part for mounting the indicator of the device needs to be closed, which is very inconvenient. In particular, operators or nurses in charge of sterilizing operations in the medical field are mostly women, and thus the opening/closing operation of such a device is not suitable for weak women.

SUMMARY OF THE INVENTION

The present invention is directed to apparatus capable of simply mounting an indicator to a device for verifying a sterilizing effect when a sterilizing process is performed.

According to an aspect of the present invention, there is provided an apparatus for installing a sterilization verifying device.

Further features and aspects of the present invention will become apparent from the following detailed description of embodiments with reference to the attached drawings.

BRIEF DESCRIPTION OF THE DRAWINGS

The accompanying drawings, which are incorporated in and constitute a part of the specification, illustrate embodiments, features, and aspects of the invention and, together with the description, serve to explain the principles of the invention.

DESCRIPTION OF THE EMBODIMENTS

Various embodiments, features, and aspects of the invention will be described in detail below with reference to the drawings.

Figure 1:
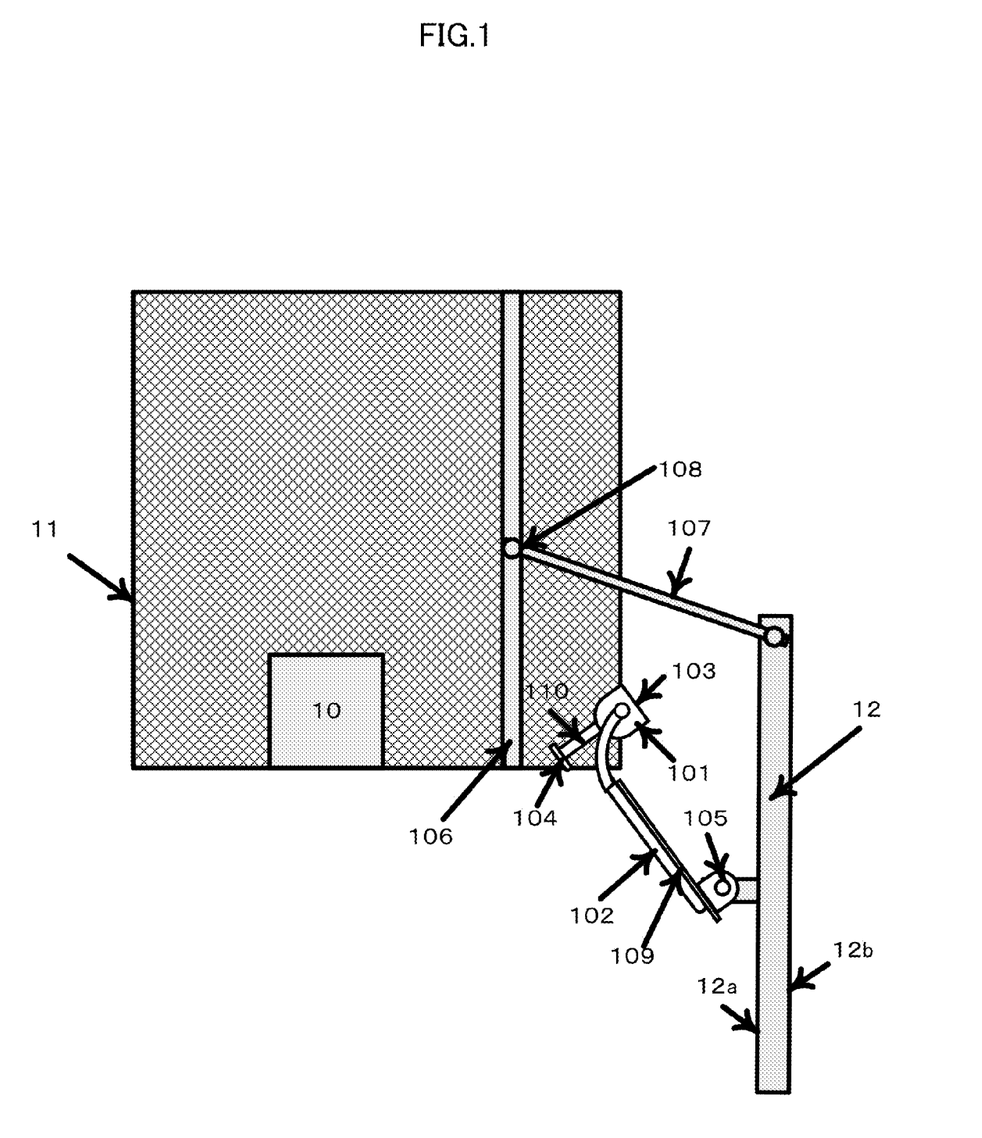
FIG. 1 is a side view illustrating a hardware configuration of an installation apparatus where a sterilization door is open.

FIG. 1 will be described. FIG. 1 is a view (side view) illustrating a hardware configuration of an installation apparatus of the present invention. FIG. 1 is a view illustrating a case where a sterilizing chamber door 12 is opened. Further, FIG. 1 illustrates that a containing chamber 101 connected to the sterilizing chamber door 12 is lowered downward (to a lowered position) as the sterilizing chamber door 12 is opened (lowered). As a result, the containing chamber 101 does not hamper a path along which an object for sterilization is carried into the sterilizing chamber 11. In addition, FIG. 1 illustrates that the containing chamber 101 connected to the sterilizing chamber door 12 is obliquely inclined as the sterilizing chamber door 12 is opened (lowered).

An effect in which the containing chamber 101 is rotated at an angle at which a user can easily introduce an indicator into the containing chamber 101 and the indicator does not drop from the containing chamber 101 can be achieved. An object for sterilization 10 may be an endoscope (a long medical instrument) with an inner cavity.

The sterilizing chamber door 12 has a square or rectangular surface (panel), and a surface facing a sterilizing chamber 11 is an inner wall 12a of the sterilizing chamber door 12. A back surface of the surface facing the sterilizing chamber 11 is an outer wall 12b of the sterilizing chamber door 12. A containing pocket (containing chamber) 101 contains the indicator.

The indicator for detecting a sterilizing effect may be contained in the containing chamber 101. Both sides of the containing chamber 101 are in communication with an introduction pipe 102. As a sterilizing gas passes through the communicated introduction tube 102, the sterilizing gas is supplied into the containing chamber 101. The introduction tube 102 has a cylindrical shape (a sealable small space) having an inner diameter of approximately 10 mm and a length of approximately 30 mm. If the indicator is contained here in advance, it is possible to verify according to a change of the indicator whether an object for sterilization is sterilized (a sterilizing effect) by the sterilizing gas passing through the indicator.

Introduction tube 102 (load tube) is preferably a Teflon (a registered trademark) tube for introducing the sterilizing gas into the containing chamber 101 to detect a sterilizing effect. The introduction tube 102 has a small inner diameter and thus functions as a resistance body (a load body) for reproducing a cavity environment of the object for sterilization 10. Further, it is useful if a metal is used for the material of the introduction tube because activity of hydrogen peroxide gas (used as the sterilizing gas) may otherwise be lost (deactivation).

An insertion part (an opening) 103 is provided such that the containing chamber is opened so that the indicator 202 may be inserted thereinto when the sterilizing chamber door 12 is opened. The containing chamber 101 and the introduction tube 102 constitute the sterilization verifying device, which is installed near the inner wall 12a of the sterilization chamber door. A pressing plate (pressing means) 104 presses the opened containing chamber 101 from the rear of the opening when the sterilizing chamber door 12 is closed, so that a contact pressure between an inner wall of the sterilizing chamber door 12 and the opening 103 may be assisted. A rotation unit (arrangement means) 105 performs rotation to cause the inner wall and the opening 103 to be brought into contact with each other when the sterilizing chamber door 12 is closed, so that the opened containing chamber 101 and the inner wall of the sterilizing chamber door 12 may be sealed.

When the sterilizing chamber door 12 is opened, the arrangement means 105 may arrange the containing chamber 101 open such that a plane including the opening 103 may be inclined relative to the plane of the sterilizing chamber door 12. Further, by additionally constituting a rotary motor control unit (an arrangement control unit) (not illustrated) in the rotation unit, it may be controlled such that when the sterilizing chamber door 12 is opened, the inner wall 12a of the sterilizing chamber door 12 and the opening 103 are not brought into contact with each other, and when the sterilizing chamber door 12 is closed, the inner wall 12a of the sterilizing chamber door 12 and the opening 103 are brought into contact with each other. Further, the degree of sealing of the containing chamber may be increased without assistance by the pressing means 104 and 106 by controlling a torque of the rotary motor unit such that a contact pressure between the inner wall 12a of the sterilizing chamber door 12 and the opening 103 is increased when the sterilizing chamber door 12 is closed.

That is, when the rotary motor control unit (arrangement control unit) is mounted, contact of the opening 103 may be controlled in conjunction with the opening/closing state of the sterilizing chamber door 12 such that the opening 103 of the containing chamber 101 connected to the sterilizing chamber door 12 and the inner wall 12a of the sterilizing chamber door 12 are not brought into contact with each other when the sterilizing chamber door 12 is opened (lowered), and the opening 103 of the containing chamber 101 connected to the sterilizing chamber door 12 and the inner wall 12a of the sterilizing chamber door 12 are brought into contact with each other when the sterilizing chamber door 12 is closed (raised). However, costs increase when an expensive rotary motor control unit (arrangement control unit) is mounted. Thus, a method of bringing the opening 103 into contact in conjunction with the opening/closing state of the sterilizing chamber door by using the inexpensive pressing plate 104 and a reference bar 106 can achieve an effect of reducing costs. In the above method, the opening 103 of the containing chamber 101 connected to the sterilizing chamber door 12 and the inner wall 12a of the sterilizing chamber door 12 are not brought into contact with each other when the sterilizing chamber door is opened (lowered), and the opening 103 of the containing chamber 101 connected to the sterilizing chamber door 12 and the inner wall 12a of the sterilizing chamber door 12 are brought into contact with each other when the sterilizing chamber door is closed (raised).

A reference bar (pressing means) 106 presses the plate 104 from the rear when the sterilizing chamber door 12 is closed, a contact pressure between an inner wall of the sterilizing chamber door 12 and the opening 103 may be provided. The location of the reference bar 106 is fixed, and as the location of the reference bar 106 is fixed, a location (distance) where the pressing plate 104 pressurizes the containing chamber 101 may be determined when the sterilizing chamber door 12 is closed. The reference bar 106 is fixed, and thus a distance between the reference bar 106 and the sterilizing chamber door 12 becomes different when the sterilizing chamber door 12 is opened and closed. When the sterilizing chamber door 12 is opened, a distance between the reference bar 106 and the sterilizing chamber door 12 becomes larger, and thus an effect of creating a space at the rear (inner wall side) of the sterilizing chamber door can be achieved.

A support bar 107 can secure an installation space at the rear. A rotation unit 108 vertically moves (elevates) the sterilizing chamber door 12. The sterilizing chamber door 12 can be automatically opened and closed while being vertically moved (elevated) by a rotation unit control unit (not illustrated). The rotation unit 108 vertically moves (elevates) the sterilizing chamber door 12 to open and close the sterilizing chamber door 12 through motor control. When the sterilizing chamber door 12 is opened, the opened containing chamber 101 may be located at a lower position than a position when the sterilizing chamber 12 is closed. Further, the rotation unit 108 serves as a supporting point of the support bar 107.

A fixing plate 109 is a plate for fixing the sterilization verifying device to prevent the sterilization verifying device from moving and causing the rotation unit 105 and the sterilization verifying device to operate in conjunction with each other. A coupling part 110 is configured to connect the rear of the containing chamber 101 and the pressing plate 104.

Figure 2:
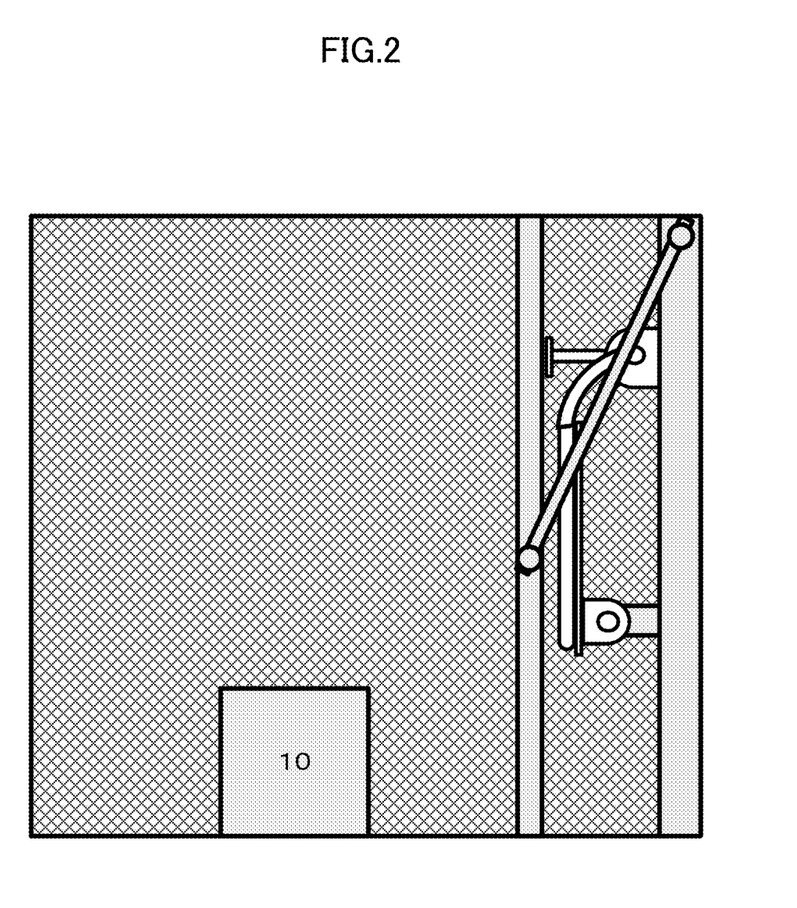
FIG. 2 is a side view illustrating the hardware configuration of the installation apparatus where the sterilization door is closed.

FIG. 2 is a side view illustrating a hardware configuration of an installation apparatus in an embodiment of the present invention. FIG. 2 is a view illustrating a case where a sterilizing chamber door 12 is closed. FIG. 2 illustrates that the opening 103 and the inner wall 12a come in contact with each other and the containing chamber 101 which is an interior environment and the sterilizing chamber 11 which is an exterior environment may be isolated from each other. Further, FIG. 2 illustrates that the containing chamber 101 connected to the sterilizing chamber door 12 is raised upward (to a higher position) as the sterilizing chamber door 12 is closed (raised).

Figure 3:
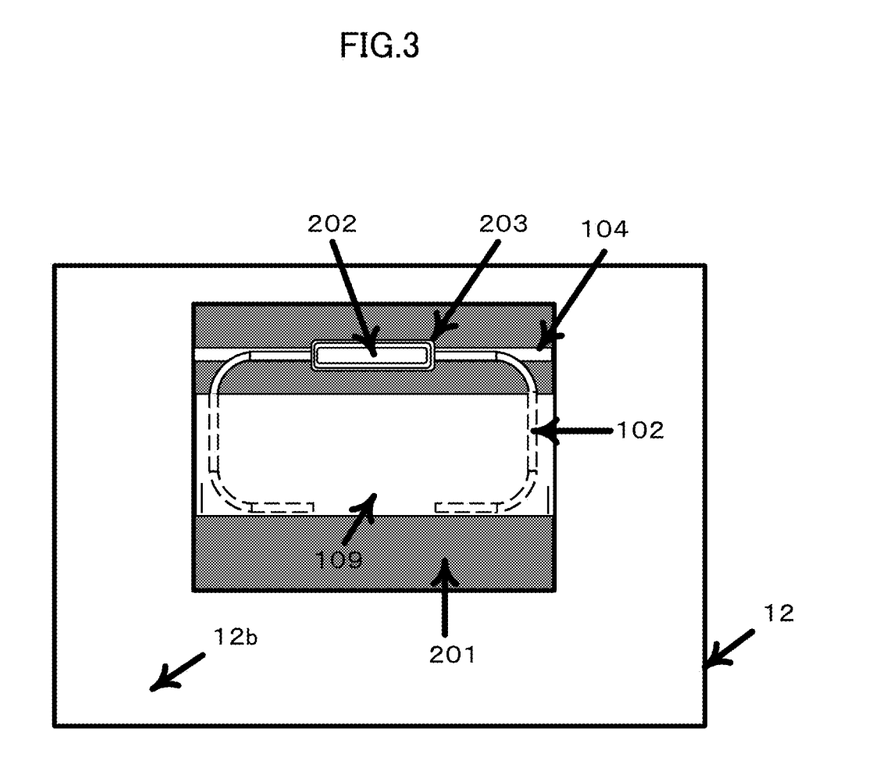
FIG. 3 is a front view illustrating the hardware configuration of the installation apparatus where the sterilization door is closed.

FIG. 3 is a front view of a hardware configuration of an installation apparatus of an embodiment of the present invention. FIG. 3 is a view illustrating a case where a sterilizing chamber door 12 is closed. FIG. 3 is a view viewed from the outside of the sterilizing chamber door 12. FIG. 3 illustrates the sterilizing chamber door 12, the rod tube (introduction tube) 102, the pressing plate (pressing means) 104, and the fixing plate 109.

A viewport (window) is installed into a hole, for example, punched in the sterilizing chamber door 12. Thus, even when the sterilizing chamber door 12 is closed, the indicator 202 already mounted into the containing chamber 101 whose opened portion is sealed may be inspected visually from an outer wall 12b (an exterior of the sterilizing chamber) of the sterilizing chamber door 12. Accordingly, a user can verify a change situation of the indicator even while a sterilizing operation is being performed by the sterilizing apparatus.

Further, the size of the window 201 may be the same size of the size (area) of the opening 103 such that only the indicator 202 may be verified, but it is useful that the size of the window 201 is larger enough that an interior space (sterilizing chamber) of the sterilizing chamber may also be viewed as illustrated in FIG. 3. When viewed from the outside of the sterilizing chamber door 12, the installation apparatus of this embodiment can be viewed through the window 201. In other words, it can be seen that the installation apparatus is present in the sterilizing chamber 11 of the sterilizing apparatus.

FIG. 3 illustrates an indicator 202 and a sealing portion 203. The member of the sealing portion employs an O-ring having a high sealing performance. When the opening 103 of the containing chamber 101 and the inner wall 12a of the sterilizing chamber door 12 come into contact each other, the containing chamber 101 which is an interior environment and the sterilizing chamber 11 which is an exterior environment may be isolated from each other by the O-ring to separate the interior environment and exterior environment of the containing chamber 101.

The reason why the installation apparatus is connected to the sterilizing chamber door 12 to be arranged near the inner wall of the sterilizing chamber door is that the sterilization verifying device is installed at a point called a cold point, where a sterilizing environment is not good (the sterilizing effect is low) in the sterilizing chamber. Thus, a sterilizing effect on an object laid at a point where a sterilizing environment is good (the sterilizing effect is high) can be achieved.

Figure 4:
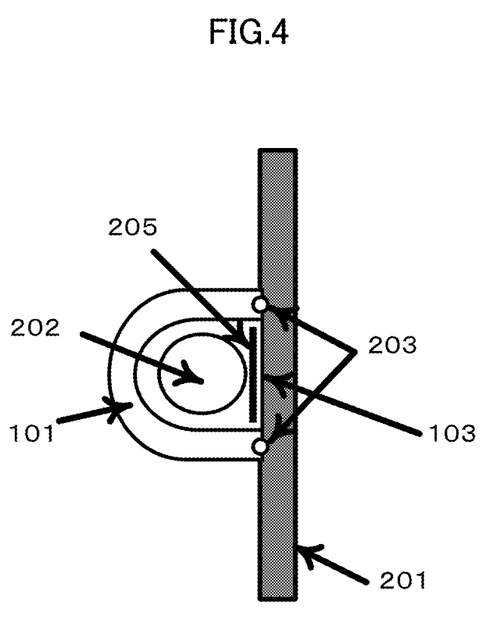
FIG. 4 is an enlarged view illustrating a containing chamber where the sterilization chamber door is closed.

FIG. 4 will be described. FIG. 4 is an enlarged view (side view) illustrating the containing chamber 101 of the installation apparatus of an embodiment of the present invention. FIG. 4 is a view illustrating a case where the sterilizing chamber door 12 is closed. FIG. 4 illustrates the containing pocket (containing chamber) 101 of the indicator, and the insertion part (opening) 103.

The viewport (window) 201 is preferably mounted by punching a hole in the sterilizing chamber door 12 and arranging the viewport window 201 therein. An indicator (BI) 202 is a "biological indicator" which uses a biological method using real germs for verifying whether an object is sterilized (sterilizing effect). FIG. 4 shows the sealing portions 203.

An indicator (CI) 205 is a "chemical indicator" which uses a chemical reaction method, for example, using litmus papers, for verifying whether an object is sterilized (sterilizing effect).

Figure 5:
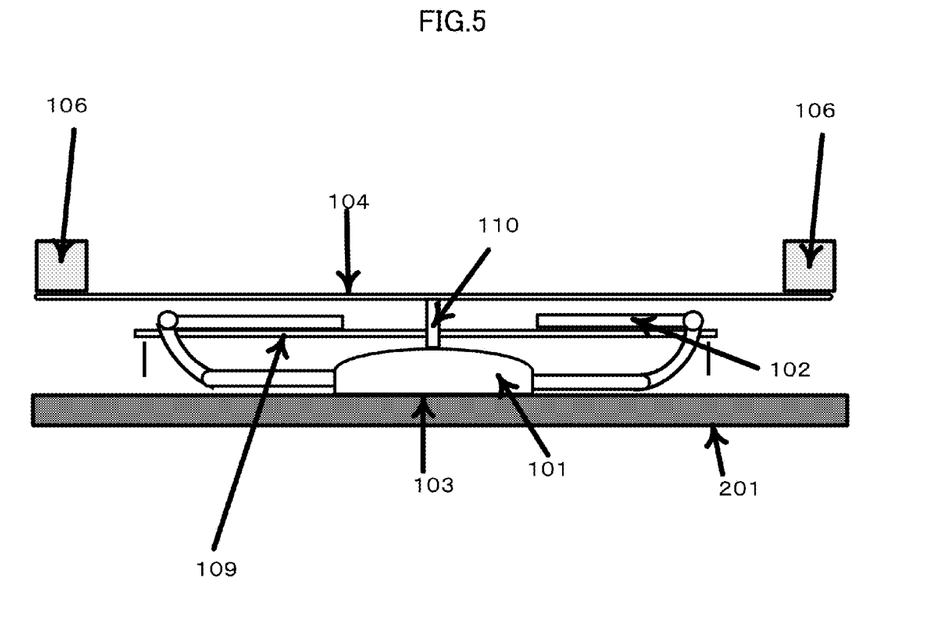
FIG. 5 is a top view illustrating the hardware configuration of the installation apparatus where the sterilization door is closed.

FIG. 5 is a top view illustrating a hardware configuration of the installation apparatus of an embodiment of the present invention. FIG. 5 is a view illustrating a case where the sterilizing chamber door 12 is closed. FIG. 5 illustrates the containing pocket (containing chamber) 101 holding the indicator. The rod tube (introduction tube) 102 may introduce the sterilizing gas supplied into the sterilizing chamber 11 into the containing chamber 101 to detect a sterilizing effect.

As the pressing plate 104 comes into contact with a reference bar (pressing means) 106, the insertion part (opening) 103 is pressed against the viewport (window) 201. FIG. 5 illustrates the fixing plate 109 and the coupling part 110. The viewport (window) 201 is mounted in a hole which has been, for example, punched in the sterilizing chamber door 12.

Figure 6:
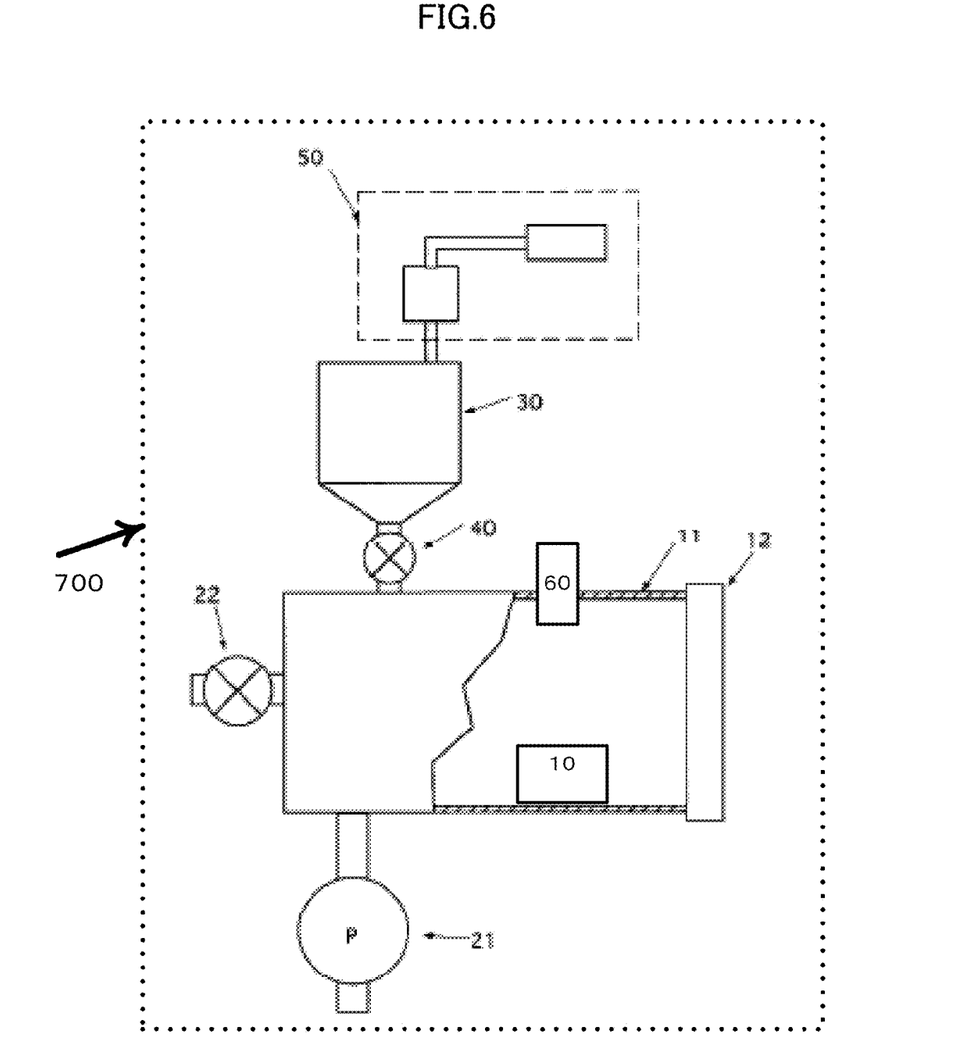
FIG. 6 is a schematic view illustrating the hardware configuration of a sterilizing apparatus including a sectional view of a sterilization chamber.

FIG. 6 is a side view illustrating a hardware configuration of a sterilizing apparatus of the present invention. FIG. 6 is a sectional view where the sterilizing apparatus 700 is viewed from the side. The object for sterilization 10 is a medical instrument to be sterilized contained in the sterilizing chamber. The object for sterilization is assumed to have an inner cavity with a complex shape.

The sterilizing chamber 11 is a housing typically having a volume of 76 liters which sterilizes a medical instrument. The interior of the sterilizing chamber 11 is a sealed space which can maintain pressure at from atmospheric pressure to a vacuum pressure. During a sterilizing operation, the temperature of the interior of the sterilizing chamber 11 is maintained at 50° C. The sterilizing chamber door 12 is a door through which a sterilizing object enters or exits from the sterilizing chamber 11. A vacuum pump 21 may control the pressure of the interior of the sterilizing chamber 11 to a vacuum pressure. In the present embodiment, a scroll dry pump without using oil is employed. This is advantageous because when an oil rotary pump is used, oil mist may blow out during an operation near the atmospheric pressure, and thus there is a need to decrease a number of rotations of the pump (increase vacuum processing time) when a vacuum processing is performed near the atmospheric pressure. As a result, when using an oil rotary pump, a vacuuming process cannot be completed in a short time.

A vaporization valve 40 is a valve capable of opening and closing a communication between a vaporizing chamber 30 and the sterilizing chamber 11. The vaporizing chamber 30 vaporizes a hydrogen peroxide liquid supplied from a hydrogen peroxide liquid supply apparatus 50. An atmospheric open valve 22 is a valve capable of opening and closing a connection between the sterilizing chamber 11 and the exterior air (the atmosphere). Further, the gas supplied to the sterilizing chamber may be not only be the exterior air but a compressed air. A hydrogen peroxide liquid supply apparatus 50 supplies a hydrogen peroxide liquid to the vaporizing chamber 30. The concentration of the hydrogen peroxide liquid supplied by the hydrogen peroxide liquid supply apparatus 50 is between 59 wt % to 98 wt %. A pressure sensor 60 measures a pressure of the interior of the sterilizing chamber 11.

Figure 7:
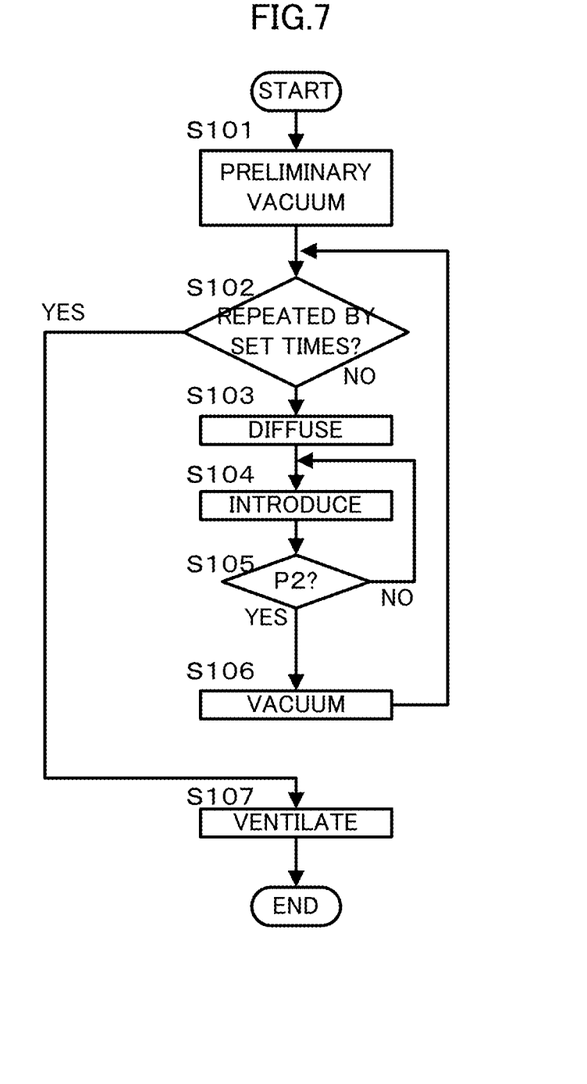
FIG. 7 is a flowchart of a sterilizing method.

A first embodiment will be described with reference to FIG. 7. FIG. 7 illustrates an embodiment of a sterilizing method (sterilizing steps) for sterilizing an inner cavity of an object for sterilization by the sterilizing apparatus. In step S101, the interior of the sterilizing chamber is maintained at a vacuum pressure by closing the atmospheric open valve 22 and operating the vacuum pump 21 (a preliminary vacuum process). In step S102, it is determined whether the process is performed after step S103 a predetermined number of times (for example, around four times) (a determination process). Specifically, it is determined how many times steps S103 to S106 are repeated. When the steps are repeated the predetermined number of times, the processing proceeds to a ventilation process of step S107.

In step S103, the vapor of the hydrogen peroxide prepared in advance in the vaporizing chamber 30, is supplied into the sterilizing chamber 11 by stopping the vacuum pump 21 and opening the vaporization valve 40 such that the vapor of the hydrogen peroxide is diffused into the interior of the sterilizing chamber (a hydrogen peroxide diffusing process). The diffusion time is a predetermined time (for example, between 60 to 480 seconds), and an interior pressure of the sterilizing chamber 11 increases during the diffusion time, and reaches a predetermined pressure P1 (first pressure) after lapse of the predetermined time. Further, in step S103, the atmosphere opening valve 22 remains closed.

In step S104, the gas (atmosphere) is supplied into the interior of the sterilizing chamber from the outside of the sterilizing chamber by opening the atmospheric open valve 22 such that the vapor of the hydrogen peroxide is introduced into an inner cavity of the object for sterilization. The introduction time is a preset time (for example, between 5 to 10 seconds), and an interior pressure of the sterilizing chamber abruptly increases during the introduction time, and reaches a predetermined pressure P2 (second pressure) after lapse of the predetermined time. Further, in step S104, the vacuum pump 21 remains stopped.

Here, it is important to introduce the vapor of hydrogen peroxide into a deep part of the inner cavity and condense the vapor of hydrogen peroxide introduced into the deep part of the inner cavity into a liquid (a hydrogen condensing process) at the same time. Thus, there is a need to abruptly increase the pressure of the sterilizing chamber up to the atmospheric pressure for a short time to condense the vapor into a liquid. The abrupt increase means that the atmosphere is abruptly supplied into the interior of the sterilizing chamber at a predetermined pressure increasing speed such that the interior pressure of the sterilizing chamber having a capacity of 76 liters and an interior pressure of 1500 Pa reaches the atmospheric pressure P2 in a short time of 5 to 10 seconds.

In addition, here, the vaporization valve 40 is closed such that the vapor of hydrogen peroxide is prepared in the vaporizing chamber 30. In step S105, it is determined by a pressure sensor for measuring an interior pressure of the sterilizing chamber whether the interior pressure of the sterilizing chamber reaches the atmospheric pressure (P2) which is a predetermined pressure. In step S106, when the interior pressure of the sterilizing chamber reaches the atmospheric pressure (P2), the interior of the sterilizing chamber at the atmospheric pressure is exhausted by closing the atmospheric open valve 22 and operating the vacuum pump 21.

In an initial process of exhausting the interior of the sterilizing chamber, as the interior pressure of the sterilizing chamber decreases (pressure reduction), the hydrogen peroxide liquid condensed in the inner cavity of the object for sterilization and having sterilized the cavity of the object for sterilization in step S104, is vaporized (evaporated) again in the inner cavity of the object for sterilization (a hydrogen peroxide vaporizing process).

It is proposed that the sterilizing effect is the greatest at the moment when the hydrogen peroxide liquid condensed in the inner cavity of the object for sterilization is vaporized again to the hydrogen peroxide vapor by the introduced gas through pressure reduction. Therefore a high sterilizing effect is not achieved by causing the hydrogen peroxide liquid condensed once to reside in the deep part of the inner cavity for a predetermined period in step S104. Thus, in order to achieve the highest sterilizing effect, the condensed hydrogen peroxide liquid may not be caused to reside for a predetermined period and the vacuuming process of step S106 may instead be started immediately.

In other words, without causing the hydrogen peroxide vapor or liquid to reside in the inner cavity of the object for sterilization for a predetermined time to increase a sterilizing effect, an instantaneously high sterilizing effect can be achieved by performing a change of a state of hydrogen peroxide, such as condensing and vaporization, by using an abrupt change in the pressure of the interior of the sterilizing chamber. In other words it becomes unnecessary to cause the hydrogen peroxide vapor or liquid to reside at the deep part of the inner cavity of the object for sterilization for a predetermined period to increase a sterilizing effect, so that an effect of starting the vacuuming process in a short time can be achieved.

The vacuum time including the initial process is a predetermined time, and during the vacuum time, the pressure of the interior of the sterilizing chamber gradually decreases, and reaches a vacuum pressure P0 after a predetermined time. The interior of the sterilizing chamber at the atmospheric pressure is exhausted by operating the vacuum pump.

The hydrogen peroxide liquid having sterilized a surface of the object for sterilization and the hydrogen peroxide liquid having sterilized the inner cavity of the object for sterilization in the interior of the sterilizing chamber, and condensed to a liquid in step S104, and the hydrogen peroxide vapor having sterilized a surface of the object for sterilization and the hydrogen peroxide vapor having sterilized the cavity of the object for sterilization in the interior of the sterilized chamber, which has been vaporized again (in step S106) may be removed (retrieved). In step S107, the interior of the sterilizing chamber is ventilated (a ventilation process). The sterilizing process is then ended.

Figure 8:
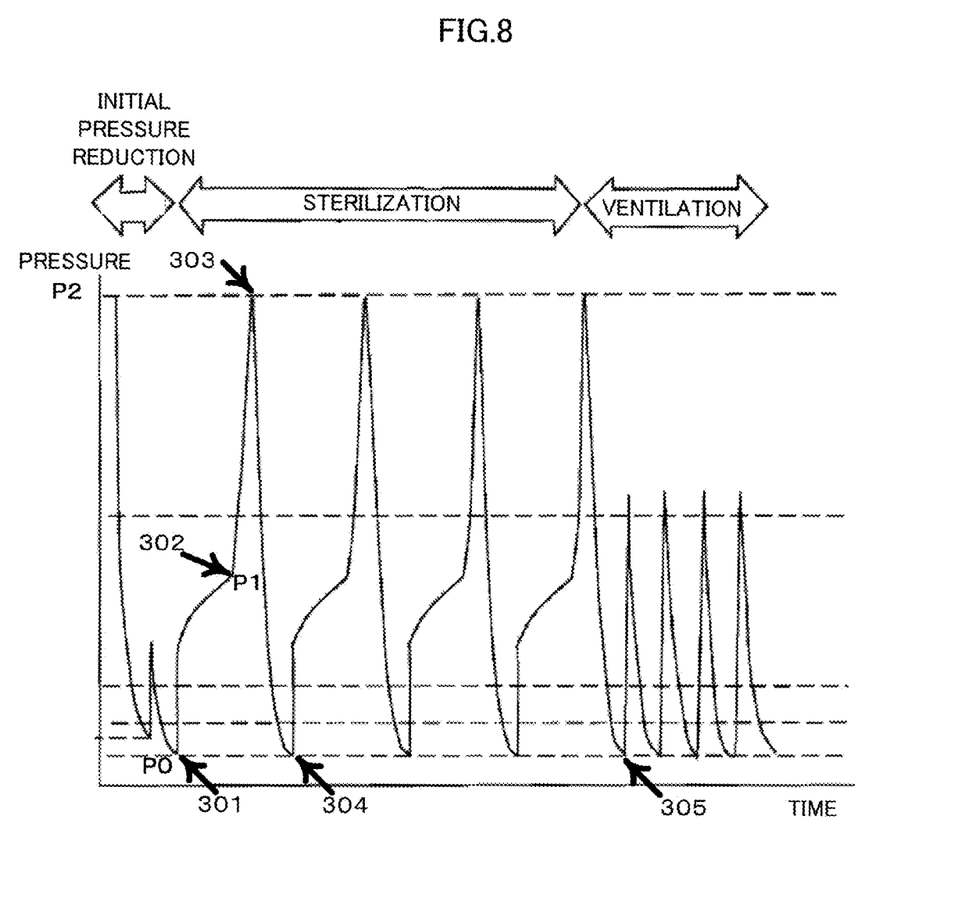
FIG. 8 is a plot illustrating changes in pressure with time in a sterilizing chamber being sterilized.

FIG. 8 illustrates a graph showing how the pressure of the interior of the sterilizing chamber changes with time during the process of the first embodiment of sterilizing the inner cavity of the object for sterilization. The pressure P0 is a pressure after the atmosphere opening valve 22 and the vaporization valve 40 are closed and the interior of the sterilizing chamber is vacuumed by the vacuum pump 21, and is a vacuum pressure between 20 Pa and 100 Pa. The pressure P1 is a pressure after the hydrogen peroxide vapor is diffused in the interior of the sterilizing chamber, and is between 1000 Pa and 4000 Pa (advantageously, 1500 Pa). The pressure P2 is a pressure after the gas (atmosphere) is supplied into the interior of the sterilizing chamber and the hydrogen peroxide vapor is condensed in the inner cavity, and is the atmospheric pressure.

Reference numeral 301 indicates a pressure (P0) before the hydrogen peroxide diffusing process of step S103 is started.

Reference numeral 302 indicates a pressure (P1) when the hydrogen peroxide diffusing process of step S103 is completed.

Reference numeral 302 indicates a pressure (P1) before the hydrogen peroxide condensing process of step S104 is started.

Reference numeral 303 indicates a pressure (the atmospheric pressure) when the hydrogen peroxide condensing process of step S104 is completed.

Reference numeral 303 indicates a pressure (the atmospheric pressure) before the hydrogen peroxide vaporizing process of step S106 is started.

Reference numeral 304 indicates a pressure (P0) when the vacuuming process of step S106 is completed.

Reference numeral 305 indicates a pressure (P0) before the ventilation process of step S107 is started.

While the present invention has been described with reference to particular embodiments, it is to be understood that the scope of protection is not limited to the described embodiments.

This application claims priority from Japanese Patent Application No. 2011-222132 filed Oct. 6, 2011, which is hereby incorporated by reference herein in its entirety.

The invention claimed is:

1. An installation apparatus for installing a sterilization verifying device in a sterilizing chamber having a sterilizing chamber door, wherein the sterilization verifying device comprises a containing chamber having an opening for receiving an object for sterilization into the containing chamber and being connected to an introduction tube for introducing a sterilizing gas into the containing chamber via the sterilizing chamber, the installation apparatus comprising:
    arrangement means configured to arrange the containing chamber such that, in a case that the sterilizing chamber door of the sterilizing chamber is opened, the opening is opened to receive an object for sterilization, and in a case that the sterilizing chamber door of the sterilizing chamber is closed, the opening is brought into contact with an inner wall of the sterilizing chamber so as to be sealed therewith,
    wherein the arrangement means moves the containing chamber such that a position of the containing chamber when the sterilizing chamber door of the sterilizing chamber is opened is in a different position from a position of the containing chamber when the sterilizing chamber door of the sterilizing chamber is closed.

2. The installation apparatus according to claim 1, wherein the arrangement means is configured to elevate the containing chamber such that the position of the containing chamber when the sterilizing chamber door of the sterilizing chamber is opened is at a lower position than the position of the containing chamber when the sterilizing chamber door of the sterilizing chamber is closed.

3. The installation apparatus according to claim 1, further comprising:
pressing means configured to press the containing chamber which is brought into contact with the inner wall of the sterilizing chamber door so that the opening is sealed in the case that the sterilizing chamber door of the sterilizing chamber is closed.

4. The installation apparatus according to claim 1, wherein the introduction tube is configured to function as a resistance body for introducing a sterilizing gas into the containing chamber.

5. The installation apparatus according to claim 1, wherein the installation apparatus is used in a sterilizing apparatus.

6. The installation apparatus according to claim 1 wherein the object for sterilization includes an indicator which can detect a sterilization result.

7. The installation apparatus according to claim 1, wherein the containing chamber is connected to the sterilizing chamber door.

8. The installation apparatus according to claim 1, wherein the arrangement means includes a function for arranging the containing chamber in conjunction with open and close operations of the sterilizing chamber door.

9. The installation apparatus according to claim 1, wherein the sterilizing chamber door further comprises a window; and
the arrangement means is further configured to arrange the containing chamber so that the opening in which an object for sterilization is inserted can be viewed through the window when the sterilizing chamber door of the sterilizing chamber is closed.

10. The installation apparatus according to claim 9, wherein the window is larger than the containing chamber.

11. An installation method for installing a sterilization verifying device in a sterilizing chamber having a sterilizing chamber door,
wherein the sterilization verifying device comprises a containing chamber having an opening for receiving an object for sterilization into the containing chamber and being connected to an introduction tube for introducing a sterilizing gas into the containing chamber via the sterilizing chamber, and
wherein the installation apparatus comprises arrangement means configured to arrange the containing chamber such that, in a case that the sterilizing chamber door of the sterilizing chamber is opened, the opening is opened to receive an object for sterilization, and in a case that the sterilizing chamber door of the sterilizing chamber is closed, the opening is brought into contact with an inner wall of the sterilizing chamber so as to be sealed therewith,
the installation method comprising causing the arrangement means of the installation apparatus to move the containing chamber such that a position of the containing chamber when the sterilizing chamber door of the sterilizing chamber is opened is in a different position from a position of the containing chamber when the sterilizing chamber door of the sterilizing chamber is closed.

* * * * *